(12) United States Patent
Schadlu et al.

(10) Patent No.: US 11,768,316 B2
(45) Date of Patent: Sep. 26, 2023

(54) ILLUMINATED CONTACT LENS AND SYSTEM FOR IMPROVED EYE DIAGNOSIS, DISEASE MANAGEMENT AND SURGERY

(71) Applicant: Preventa Medical Corporation, Phoenix, AZ (US)

(72) Inventors: Ramin Schadlu, Phoenix, AZ (US); Zhijie Chen, Stanford, CA (US)

(73) Assignee: Preventa Medical Corporation, Phoenix, AZ (US)

( * ) Notice: Subject to any disclaimer, the term of this patent is extended or adjusted under 35 U.S.C. 154(b) by 973 days.

(21) Appl. No.: 16/601,442

(22) Filed: Oct. 14, 2019

(65) Prior Publication Data

US 2020/0116897 A1 Apr. 16, 2020

Related U.S. Application Data

(60) Provisional application No. 62/865,036, filed on Jun. 21, 2019, provisional application No. 62/745,284, filed on Oct. 13, 2018.

(51) Int. Cl.
*G02B 1/04* (2006.01)
*G02C 7/04* (2006.01)
(Continued)

(52) U.S. Cl.
CPC .............. *G02B 1/043* (2013.01); *A61B 3/063* (2013.01); *A61B 5/0022* (2013.01);
(Continued)

(58) Field of Classification Search
CPC .... G02B 1/043; G02B 27/0138; G16H 40/67; A61B 3/063; A61B 5/0022; A61B 5/6821; G02C 7/049
See application file for complete search history.

(56) References Cited

U.S. PATENT DOCUMENTS 3,630,602 A 12/1971 Herbert
3,944,341 A 3/1976 Pomerantzeff
(Continued)

FOREIGN PATENT DOCUMENTS

KR 10-2013-0076079 A 7/2013
WO 2017191375 A1 11/2017

OTHER PUBLICATIONS

European Search Report, EP Patent Application No. 19871041.0, dated Aug. 8, 2022, 13 pages.
(Continued)

*Primary Examiner* — William R Alexander
*Assistant Examiner* — Sharrief I Broome
(74) *Attorney, Agent, or Firm* — IPTechLaw (57) ABSTRACT

A new ocular contact lens has been designed to increase the amount of light reaching the retina. The contact lens edge is chamfered to redirect and increase the light reaching the retina. A light source encircles and contacts the straight or curved chamfered edge. Additionally, a reflective cylinder and its top wall encircle the lens to block any loss of light. This distal edge of the contact lens may be rounded to increase the angle of retina visible. A new ocular imaging camera has a low-light camera subassembly with server, a photosensor next to low-light camera, a short cylindrical housing, a space between the camera subassembly and the housing, an internal program in server to detect good or poor image quality and an alarm for poor image quality, wherein an operator recaptures the image. A system has a highly efficient method to screen and diagnose a large number of patients using the new ocular contact lens and ocular imaging camera. The system receives and processes the photographs. The photographs are transmitted to eye care specialists' smart phone, tablet or virtual reality device for evaluation. As specified, the eye care specialist separates
(Continued)

normal from abnormal, diagnoses the abnormality, and may even provide detailed information, such as the grade of the abnormality. The server receives this information and automatically generates the suitable report for the healthcare professional. The server also processes payment to the eye care specialist.

20 Claims, 9 Drawing Sheets

(51) Int. Cl.
  *A61B 5/00* (2006.01)
  *G16H 40/67* (2018.01)
  *A61B 3/06* (2006.01)
  *G02B 27/01* (2006.01)
(52) U.S. Cl.
  CPC ............ *A61B 5/6821* (2013.01); *G02C 7/049* (2013.01); *G16H 40/67* (2018.01); *G02B 2027/0138* (2013.01)

(56) References Cited

U.S. PATENT DOCUMENTS

| | | | |
|---|---|---|---|
| 4,007,980 A | | 2/1977 | Bracher et al. |
| 4,598,984 A | | 7/1986 | Rol |
| 4,810,082 A | * | 3/1989 | Abel, Jr. ................ G02C 7/04 351/159.67 |
| 5,501,217 A | * | 3/1996 | Ishiguro ................. G02C 7/04 351/200 |
| 5,822,036 A | | 10/1998 | Massie et al. |
| 6,164,779 A | * | 12/2000 | Volk ...................... A61F 9/009 351/219 |
| 6,221,028 B1 | | 4/2001 | Lieberman et al. |
| 6,766,042 B2 | | 7/2004 | Freeman et al. |
| 8,677,282 B2 | | 3/2014 | Cragun et al. |
| 8,826,128 B2 | | 9/2014 | Reynolds et al. |
| 8,876,284 B2 | | 11/2014 | Legerton |
| 9,075,903 B2 | | 7/2015 | Marshall et al. |
| 9,179,840 B2 | | 11/2015 | Su |
| 9,613,325 B2 | | 4/2017 | Sorkey et al. |
| 9,770,167 B2 | | 9/2017 | Yetik |
| 9,801,540 B2 | | 10/2017 | Yates |
| 9,946,841 B2 | | 4/2018 | Jun et al. |
| 2004/0196434 A1 | * | 10/2004 | Khaw .................. A61B 3/117 351/219 |
| 2005/0041200 A1 | | 2/2005 | Rich |
| 2010/0091244 A1 | * | 4/2010 | Volk .................... A61B 3/117 351/219 |
| 2014/0252667 A1 | * | 9/2014 | Van Dijk ............. B29D 11/023 351/159.02 |
| 2015/0302146 A1 | | 10/2015 | Marshall et al. |
| 2016/0183782 A1 | | 6/2016 | Yu et al. |
| 2016/0249804 A1 | | 9/2016 | Wang |
| 2017/0354326 A1 | | 12/2017 | Pugh et al. |
| 2018/0035879 A1 | | 2/2018 | Kumar et al. |
| 2018/0064505 A1 | | 3/2018 | Zhao et al. |
| 2018/0108442 A1 | | 4/2018 | Borve |
| 2018/0110647 A1 | | 4/2018 | Lee et al. |
| 2018/0344154 A1 | | 12/2018 | Svetliza et al. |

OTHER PUBLICATIONS

Volk Optical Inc., The Finest Ophthalmic Imaging, Oct. 6, 2017, Retrieved from the Internet on Apr. 25, 2019: https://volk.com/media/wysiwyg/pdf/brochures/Volk-Product-Catalog.pdf, 48 pages.
Lee, W.W., Ophthalmology Web—Choosing a Gonioscope, Nov. 29, 2011, Retrieved from the Internet on Apr. 25, 2019: https://www.ophthalmologyweb.com/Tech-Spotlights/36495-Choosing-a-Gonioscope/, 2 pages.
Griffith, C., WVU Doc Develops New App to Help Detect Skin Cancer, State Journal News, Sep. 10, 2018, Retrieved from the Internet on Apr. 25, 2019: https://www.wvnews.com/statejournal/news/wvu-doc-develops-new-app-to-help-detect-skin-cancer/article_310a1b7c-d074-57bb-8f2e-a681b4b0aa68.html, 4 pages.
Software Advice, iPad EMR Software, Apr. 1, 2019, Retrieved from the Internet on Apr. 26, 2019: https://www.softwareadvice.com/medical/tablet-pc-emr-medical-software-comparison/, 12 pages.
International Search Report, PCT Patent Application No. PCT/US2019/056148, dated Sep. 17, 2020, 5 pages.

* cited by examiner

ILLUMINATED CONTACT LENS AND SYSTEM FOR IMPROVED EYE DIAGNOSIS, DISEASE MANAGEMENT AND SURGERY

GOVERNMENT LICENSE

This invention was made without government support. The government has no rights in this invention.

CROSS REFERENCE TO RELATED APPLICATIONS

Related applications include U.S. Provisional Application Ser. No. 62/865,036 filed Jun. 21, 2019, still pending; and U.S. Provisional Application Ser. No. 62/745,284 filed Oct. 13, 2018, still pending. Both applications are incorporated by reference.

BACKGROUND

Technical Field

Implementations of the illuminated contact lens assemblies relate to lens assemblies used with an ocular imaging camera. Particular implementations also include a reflector and a light source to illuminate the anterior and posterior segment of a patient's eye. These devices are used in a rapid diagnosis system.

BACKGROUND

Visual impairment interferes with the ability to earn a living and quality of life through the loss of reading ability, computer operation, walking, socializing and operating vehicles. Conventionally, causes of blindness have been diagnosed by ophthalmologists after primary healthcare practitioners refer patients who complain of vision problems and loss of function, such as difficulty reading or driving. Globally, the World Health Organization reports that the most common cause of blindness is cataracts, followed by age-related macular degeneration and diabetic retinopathy. Most severe vision loss occurs in individuals older than 50. Therefore, it is vital that earlier diagnosis avoids these developments. Included in the list of retinal disorders are diabetic and/or hypertensive damage and age-related macular degeneration (AMD), which is a leading cause of blindness in the United States and other industrialized countries. It is a leading cause of vision loss in individuals over 50. By age 80 most individuals with the disorder experience some vision loss.

The macula is a small portion of the retina in the rear of the eye and is critical to high acuity vision. When an individual turns the head to focus on an object, the macula is being centered onto the object. When the macula is damaged, only peripheral vision remains and central acuity is lost.

Hypertension and diabetes damage small blood vessels, including those in the retina. In diabetes, the weak blood vessels underlying the retina bleed and set up an inflammatory reaction and scarring of the retina if not treated promptly.

About 80% of AMD cases are "dry" or atrophic with a slow loss of retinal pigment epithelium and photoreceptors (responsible for vision). Later stages are either late-stage dry AMD or wet AMD. Because of the aging population, there are estimated to be about 288 million cases by 2040.

Another leading cause of blindness is diabetic retinopathy, which accounts for 12% of all new cases of blindness. Importantly for people aged 20-64, it is the leading cause of blindness. Diabetic retinopathy will occur in 80% of people having diabetes for 20 or more years. It often has no early warning symptoms; however, retinal photography can pick up early stages, such as the appearance of microaneurysms, retinal hemorrhages and vascular anomalies such as "beading" of the retinal veins and other microvascular abnormalities. Varying degrees of vision loss occurs in eyes affected by associated leakage of serous fluid and cholesterol into the retina, a complication known as macular edema. In the late stages, anomalous blood vessels grow out of the retina in an unregulated fashion causing bleeding. Scar tissue accompanying these vessels can cause irreversible vision loss from retinal detachment. All aforementioned stages can be easily imaged photographically In the UK, screening of diabetics for any of these signs is standard care. Earlier screening permits earlier treatment and prevention of needlessly advanced stages. Simple interventions such as improved glucose control, correction of hypertension and cholesterol control can help avoid or delay advanced stages of diabetic retinopathy.

Hypertension alone can lead to hypertensive retinopathy in which the blood vessels are initially involved. The small arterioles narrow either focally or generally. There can be "nicking" of the veins by the arterioles. Later, there can be bleeding and "cotton wool spots" (ischemic areas) and vision loss. Even before the blood pressure rises significantly, hypertensive retinopathy can be seen in about 3-14% of adults over 40 years old. In addition, dozens of other less common diseases can have ocular manifestations.

Many patients arrive in the retina specialist's office with advanced stages of hypertension, diabetic retinopathy, AMD, etc. As established in many studies such as the ETDRS (Early Treatment Diabetic Retinopathy Study), DRS (Diabetic Retinopathy Study) and PANORAMA Study, earlier diagnosis translates into preservation of vision, higher quality of life, decreased burden to the healthcare and disability systems, and increased productivity. As a result of aging of the tens of millions of additional AMD patients projected for the near future, increased capacity and efficiency are sorely needed given an anticipated shortage of eye care providers (ophthalmologists and optometrists) as a result of the inefficiencies of a traditional eye exam that we have identified.

SUMMARY

In one embodiment, there is disclosed an ocular contact lens that includes a) a proximal curved surface to contact the surface of the eye; b) a distal flat surface through which the retina can be seen; c) partially chamfered sides of the ocular contact lens wherein the sides have a narrower circumference closer to the flat distal surface and wider near the proximal curved surface; and d) partially straight sides of the ocular lens (perpendicular to the flat surface) that extend from the proximal surface to the chamfered side.

Optionally, the ocular contact lens has at least one of glass, polymers, poly(methyl) methacrylate, and plastics. The ocular contact lens has the angle of the chamfered edges at an angle of about 0° to about 90°. The chamfered edge can be straight or curved. Preferably the angle of the chamfered edge is about 45°. Alternately the distal somewhat flat surface ("flat surface") can be slightly rounded to widen the view through the contact lens and capture a wider angle of the retina. The maximum feasible angle of the ocular contact lens material is determined by Θ<180-2*arcsin(1/n), wherein n is the refractive index of the material. The ocular contact lens thickness is about 0.25 mm to 2.75 mm. Alternately, the ocular contact lens thickness is about 2.75 mm to about 10 mm.

In another embodiment, an ocular contact lens assembly has a) a proximal curved surface to contact the surface of the eye; b) a distal flat surface through which the retina can be seen; c) chamfered edge wherein the contact lens has a narrower circumference at the distal surface and a wider circumstance closer to the curved surface; d) partially straight edge of the ocular contact lens (perpendicular to the flat surface) that extends from the curved surface to the chamfered edge; and e) a light source circling and contacting at least a portion of the chamfered sides, the light source having a toroidal cross section.

Optionally, the ocular contact lens assembly has an angle of the chamfered contact lens edge of about 0° to about 90°. The angle of the chamfered contact lens can be about 45°. The distal contact lens surface of the ocular contact lens assembly can be slightly rounded to widen the view through the contact lens and capture of a wider angle of the retina. The maximum feasible angle of a material is determined by Θ<180-2*arcsin(1/n), wherein n is the refractive index of the material. The ocular contact lens thickness may range from about 0.25 mm to 2.75 mm. Alternately, the ocular contact lens thickness is about 2.75 mm to about 10 mm. The chamfered edge can be straight or concave. The ocular contact lens assembly includes at least one of glass, polymers, poly(methyl) methacrylate, plastics, fiber optics, reflective materials and LED's. The ocular contact lens assembly also can have a cylindrical reflector facing the chamfered edge of the contact lens and enclosing the light source, thereby preventing more light from escaping the ocular contact lens assembly. The ocular contact lens assembly can also have a top wall over the cylindrical reflector, extending from the cylindrical reflector to the side of the ocular contact lens. The ocular contact lens assembly reflective material can be a mirror or coated surface.

In yet another embodiment, there is disclosed an improved system for screening and diagnosing a large number of patients' eyes, the system comprising a) an ocular contact lens contacting an eye; b) a light source; c) a camera positioned over the ocular contact lens and connected to a server; d) a server programmed to receive and process photographs from the camera and send them to selected eye care specialists' mobile devices; e) the mobile devices displaying photographs of eyes, receiving swipe messages to indicate eye status, receiving commands from the eye expert; f) the server translates the eye expert commands into communications to the health care professional and optionally the patient; g) the server is programmed to pay the eye care specialist; and h) the server is programmed to send processed photographs to the eye care specialist.

Optionally, the mobile device displays a symbol for a swipe gesture, information and lock, whereby a swipe, tap or other gesture sends a signal that the photograph is normal. When actuated the lock keeps the same photograph for enlarging or moving back and forth. The mobile device includes but is not limited to a smart phone, a tablet, and a virtual reality device. The screening system may have a program for presorting photographs into normal, and abnormal. The ocular contact lens may have chamfered edges on which a light source is positioned. The ocular contact lens may have chamfered edges, a light source, and a reflective cylinder with a top wall extending to the edge of the ocular contact lens.

In yet another embodiment, an ocular imaging camera includes a low-light camera subassembly with minicomputer, a photosensor next to a low-light camera, a short cylindrical housing, a space between the camera subassembly and the housing, a light at the front of the housing, an internal program in minicomputer to detect good or poor image quality; and an alarm for poor image quality. Optionally, the low-light camera subassembly includes the light and the photosensor.

The foregoing and other aspects, features, and advantages will be apparent to those artisans of ordinary skill in the art from the DESCRIPTION and DRAWINGS, and from the CLAIMS.

BRIEF DESCRIPTION OF THE FIGURES

Implementations will hereinafter be described in conjunction with the appended drawings, where like designations denote like elements, and:

FIG. 15 shows side by side photos of two retinas. FIG. 15-1 shows a retina labeled no pathology. FIG. 15-2 shows a retina labeled with pathology.

DETAILED DESCRIPTION

After much thought and experimentation, we invented a method to create a much more efficient way for connecting the primary practitioner and the eye care specialist for earlier eye diagnosis. This method enables a retina specialist, ophthalmologist, optometrist, etc. (eye care specialist) to diagnose and triage hundreds of patients per hour.

First, we have invented a special illuminated contact lens that is designed to make the front-line healthcare professional's lens placement and photography simpler and more effective. We also describe an improved ocular imaging camera, also designed for ease of use by healthcare professionals. We further link obtaining the photo with a system (described below) with certified eye care specialists. Although the three parts are synchronized to produce a new paradigm in healthcare, each of the parts can be used with other medical devices or systems, which they can be expected to improve the patient results. The three parts are described below.

New Contact Lens with Integral Light Source

Adequate illumination is a vital part of ophthalmology and presents a challenge, because various parts of the eye, including the pigmented epithelium layer or inner surface of a mammalian eye, have very low reflectivity. Any stray light reflected from the interface between air and the most distal phase of vitreous humor can significantly distort the view of the intraocular space. These illumination challenges affect both ocular imaging and intraocular surgeries. For example, in intraocular surgeries one or more intraocular illumination probes are inserted into the sclera, the protective outer layer of the eye, to deliver light directly to the retina to increase visibility within the eye. These light probes are expensive and require an invasive entry into the eye.

In retinal imaging, a specialized low power microscope with an attached camera is designed to photograph the interior surface of the eye (i.e. the fundus), including the retina, retinal vasculature, optic disc, and macula. Current techniques for retinal imaging include using anti-reflection (AR) coating on the glass of the lens used in the camera. Even with the anti-reflection coating, reflection from the cornea still presents a challenge in clearly viewing the inner portions of the eye. Many fundus camera designs separate the illumination light path and the imaging path spatially. This design results in a smaller clear aperture for imaging, which limits the image quality.

Figure 1:
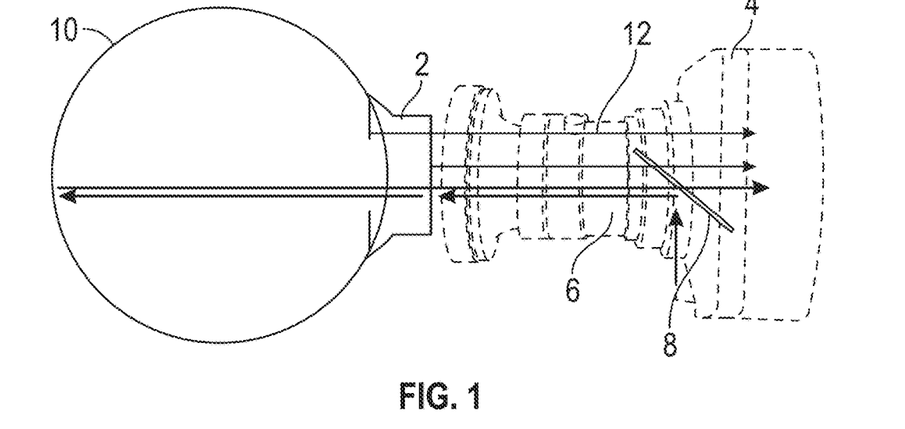
FIG. 1 is a schematic cross section of an eye with a typical flat ocular contact lens thereon and a known camera next to it.

Referring to FIG. 1, a schematic of a currently used flat lens 2 with a fundus camera is illustrated. The desired path of the light 6 is to enter through the flat lens 2 and go to the back of the eye. The light from a light source below the camera is directed into a beam splitter 8 and then reflected into the eye 10. However, as illustrated by the green line, stray light 12 bounces off the surface of the flat lens even with AR coating. The stray light 12 can also bounce from the inner curves of the flat lens as will be further explained below.

Figure 2:
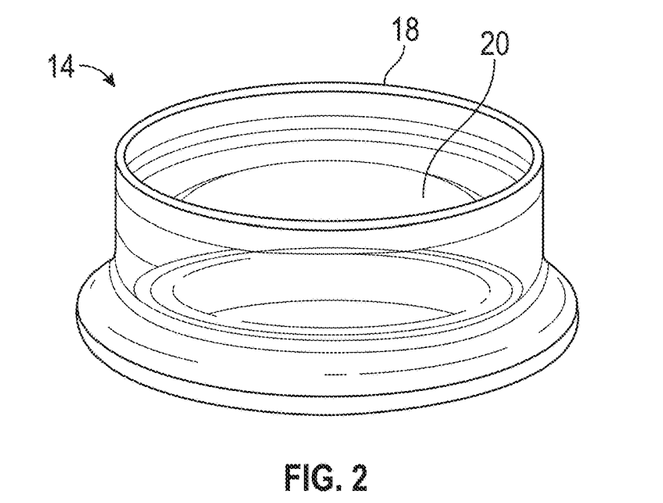
FIG. 2 is a schematic overview of a currently marketed ocular lens.
Figure 3:
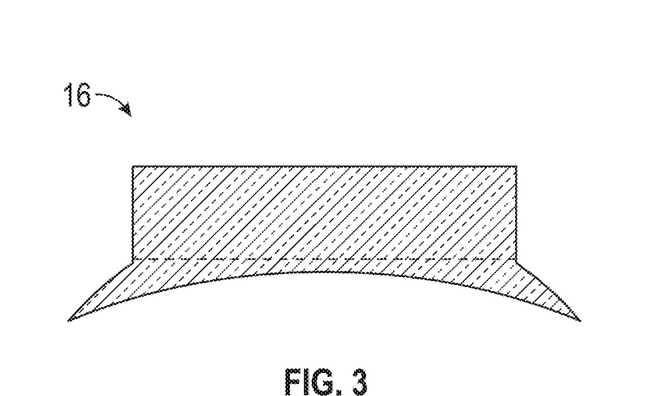
FIG. 3 is a schematic cross section of a current flat lens.

Referring to FIG. 2, a currently used flat lens 14 is illustrated. This particular lens is manufactured by Dutch Ophthalmic Research Center (D.O.R.C.) B.V., a limited liability company of Zuidland, The Netherlands. A flat lens is an optical component applied on the cornea to cancel a majority of the dioptric power of the human eye. The flat lens can provide a clear view of the intraocular space of the eye. In FIG. 3, a cross sectional view of a current flat lens 16 is illustrated. This particular lens has a diameter of 12 mm. Referring again to FIG. 2, the lens is flat on the surface 18 distal to the human eye when the lens is on the eye. Within the lens, the proximal curvature 20 of the lens is visible. The curvature is shaped to rest on the human eye to provide the best imaging of the retina and fundus of the eye. The many surfaces and curves of the lens can increase the amount of stray light produced.

Without being tied to any one theory, various implementations of flat lens assemblies as described herein may work based on total internal reflection (TIR). TIR is the phenomenon that involves the reflection of all the incident light off the boundary of a surface. TIR only takes place when two conditions are met: the light is in the denser medium and approaching the less dense medium and the angle of incidence is greater than the so-called critical angle. Total internal reflection only occurs with large angles of incidence. For example, large angles of incidence may be any angle greater than 48o when light is reflected between air and water. For other media or materials the angle may be determined using the formula $\Theta = \arcsin(n2/n1)$, where n1 is the refractive index of the more dense medium and n2 is the refractive index or the less dense medium.

Implementations of contact lens assemblies as described herein are designed to improve retinal imaging and intraocular surgeries through optimized delivery of light to the retina in a non-invasive and non-traumatic way. In various implementations of contact lens assemblies, there are no components in front of the lens and proximal to the eye. This may increase the field of view of the lens up to the limitation of the pupil and may avoid geometrically interfering with other devices. Lastly, various implementations of contact lens assemblies eliminate most stray light since little light escapes from the distal surface of the flat lens before being reflected back to the retina. We have designed the contact lens to transmit more light ways and reduce light scatter.

Figure 4:
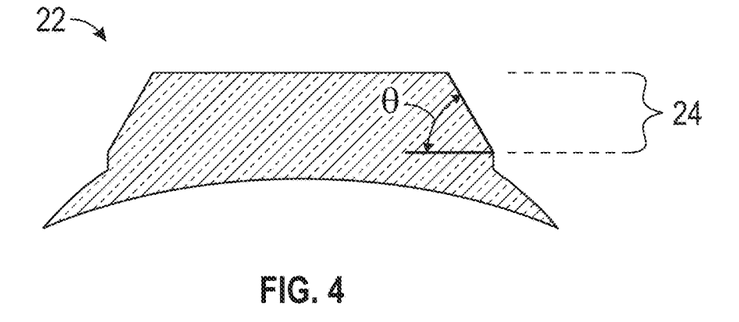
FIG. 4 is a schematic cross section of an embodiment of the chamfered ocular contact lens.

Referring to FIG. 4, an implementation of a cross sectional view of a contact lens 22 having a chamfered cut is illustrated. A circular chamfer is cut off from the top corner of the contact lens. The chamfer cut can be straight or produce a curved edge (concave or convex). In various implementations, the chamfer 24 can be cut from a standard contact lens. In some implementations, the contact lens can be cut through laser, diamond, blade, or other methods of cutting glass to provide a clean cut. In other implementations, the contact lens may be formed with a chamfered edge through molding or other techniques. The contact lens is cut at an angle $\Theta$ of 45o. In other implementations, the angle may range from 0o-about 90o. In various implementations, depending on the material of the contact lens, the maximal feasible angle may be determined using the formula $\Theta < 180 - 2*\arcsin(1/n)$ where n is the refractive index of the material. The thickness of the contact lens may range from 0.25 mm to 2.75 mm in various implementations. The contact lens may be thicker (2.75 mm to about 5 or 10 mm) in new uses.

Figure 5:
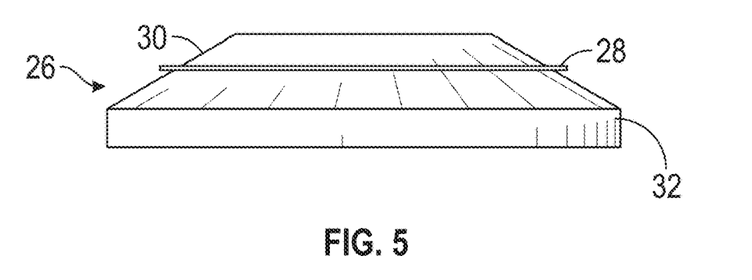
FIG. 5 is a schematic side view of an ocular contact lens assembly with a light source thereon.

Referring to FIG. 5, a side view of an implementation of a contact lens assembly 26 is illustrated. In this implementation, the flat lens assembly 26 includes a light source 28. The light source is illustrated coupled around the perimeter of the chamfered edge 30 of the contact lens 32. The flat lens 32 is illustrated. As illustrated, the light source 28 has a toroidal shape. The toroidal shape of the light source 28 gives a continuous light source. The light source 28 may include a fiber optic loop in various implementations. The fiber optic loop surface is deformed to provide for random locations of light. The placement of the light source 28 reduces stray light since a beam of light is not directly hitting the outer surface of the contact lens from outside the contact lens as illustrated in the current model in FIG. 1. Rather, the light directly contacts the surface of the lens from the inside and is reflected back to illuminate the retina following the principles of TIR. In other implementations, light emitting diode (LED) lights are used as the light source. An LED light source provides discrete points of light.

Figure 6:
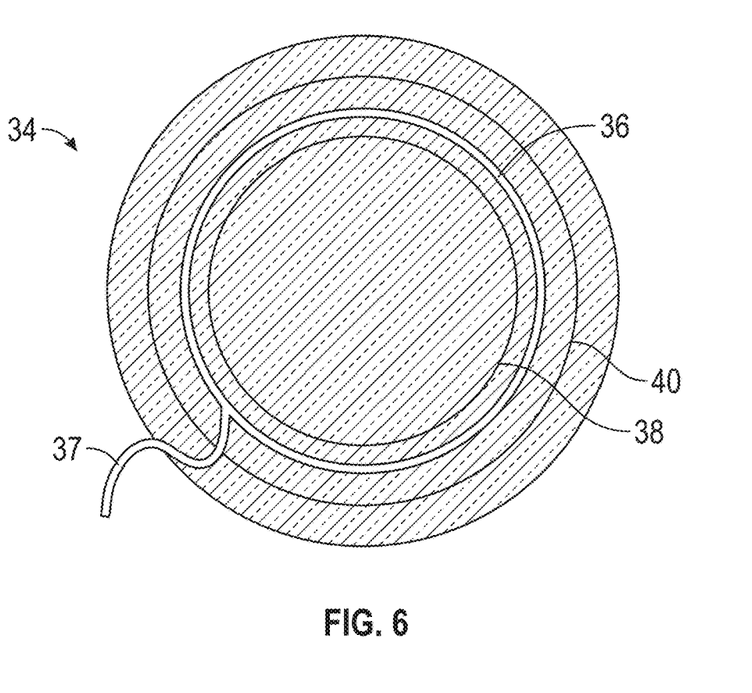
FIG. 6 is a schematic top view of a contact lens assembly showing the chamfered edge and light source.
Figure 7:
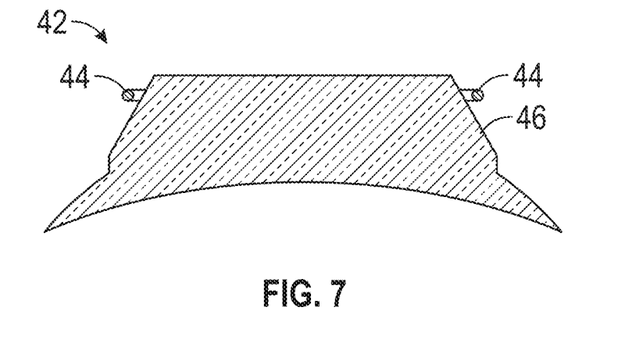
FIG. 7 is a schematic cross-section of the contact lens assembly with the light source coupled to the chamfered edge.

Referring to FIG. 6, a top view of an implementation of a contact lens assembly 34 is illustrated. The light source 36 is illustrated and is located on the chamfered edge of the contact lens. The light source 36 is configured to be coupled to an external light source through additional optical fiber 37 as illustrated. The distal top 38 and proximal bottom 40 edges of the chamfered edge are illustrated by two concentric circles. Referring to FIG. 7, a schematic of a cross section of the contact lens assembly 42 with the light source 44 coupled to the chamfered edge 46 is illustrated.

Figure 8:
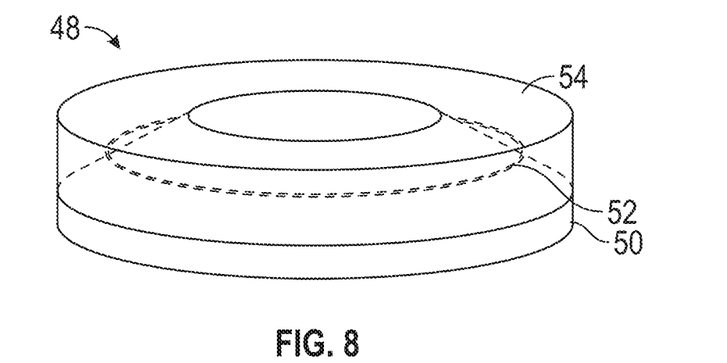
FIG. 8 is a view of the ocular contact lens assembly with a cylindrical reflector coupled to the edge of the contact lens.

Referring to FIG. 8, an implementation of a contact lens assembly 48 including the contact lens 50, light source 52, and reflector 54 is illustrated. A reflector is coupled to the contact lens on the straight edge close to the chamfered edge. In various implementations, the reflector 54 may be formed a mirrored material where the mirror faces the light source. In other implementations, a first surface of the reflector 54, facing the chamfered edge of the contact lens, has a reflective surface. The reflector comprises a reflecting material or has a coated surface or reflective material coupled to the inner side of the reflector. The outside of the chamfered edge may also be coated. The reflector 54 encloses the light source to form a chamber having a circular shape around the chamfered edge and the light source of the flat lens assembly. The reflector helps retain even more reflected light inside its chamber.

Figure 9:
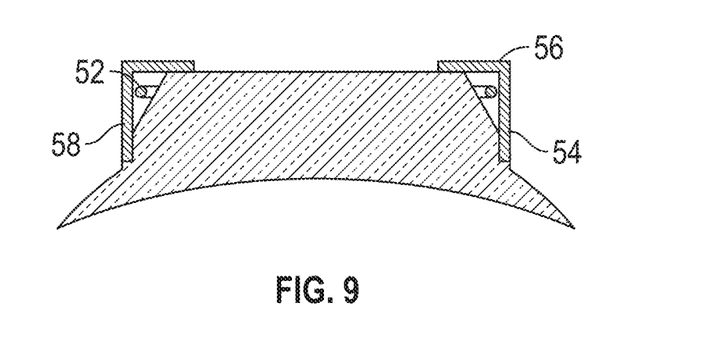
FIG. 9 is a schematic cross sectional view of the contact lens assembly showing the cylindrical reflector with a top wall encompassing all of the chamfered section of the contact lens.

Referring to FIG. 9, a schematic of a cross sectional view of the contact lens assembly of FIG. 8 is illustrated. In this view, the side wall 58 and the top wall 56 of the reflector 54 are illustrated. As illustrated, the light source 52 is completely enclosed within the top wall 56 and side 58 of the reflector 54, for even greater retention of light for the ocular photograph.

Figure 10:
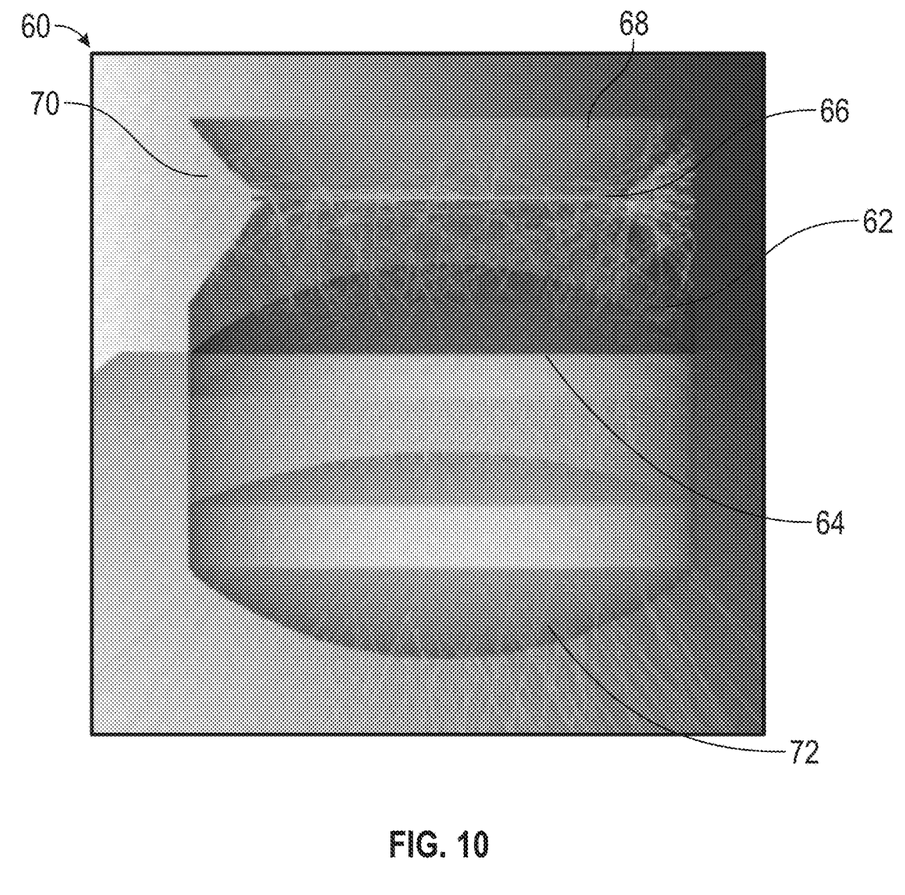
FIG. 10 is a schematic of a model of the total internal reflection (TIR) applied to the ocular contact lens.

Referring to FIG. 10, a model of the total internal reflection (TIR) when using an implementation of a contact lens assembly 60 is illustrated. The contact lens 62 is illustrated coupled with a spherical surface 64 similar to a human eye. The light source 66 is illustrated coupled around the chamfered edge of the contact lens 62. The reflector 68 is illustrated coupled to the flat edge of the contact lens. In this particular view, the side walls of the reflector are not illustrated to increase visibility of the reflection of the light rays 70 within the chamber of the reflector. Light rays 70 are illustrated as thin, scattered lines throughout the model. Total internal reflections results in essentially all light reflecting back upon its first arrival on the distal interface of the contact lens 62 including the clear central part on the frontal planar surface of the contact lens. As previously explained, there is an upper-bound angle $180-2*\arcsin(1/n)$ for the chamfer cut. Any angle less than that would work in the sense of eliminating stray light. The optimal angle varies depending on the contact lens material/light source angular profile. Due to the reflective surface of the reflector, all light should also bounce off the reflector.

Figure 11:
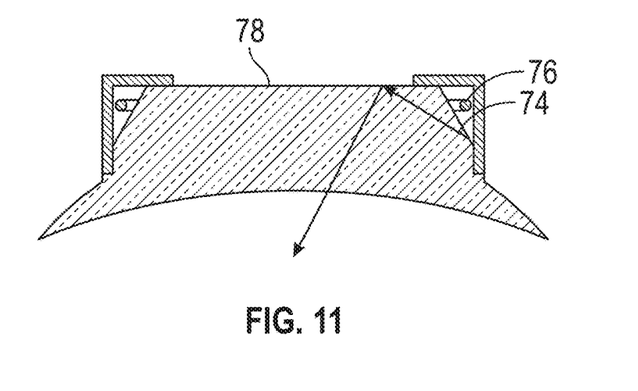
FIG. 11 is a schematic of the model in FIG. 10 showing the path of a single ray of light.
Figure 12:
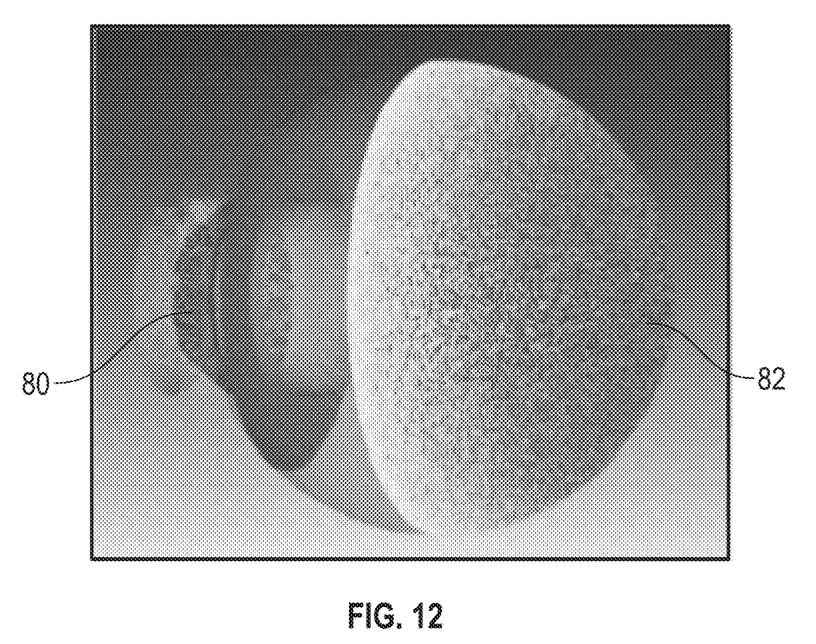
FIG. 12 is another representation of the model, showing the small contact lens on the left and the large retina on the right.
Figure 13:
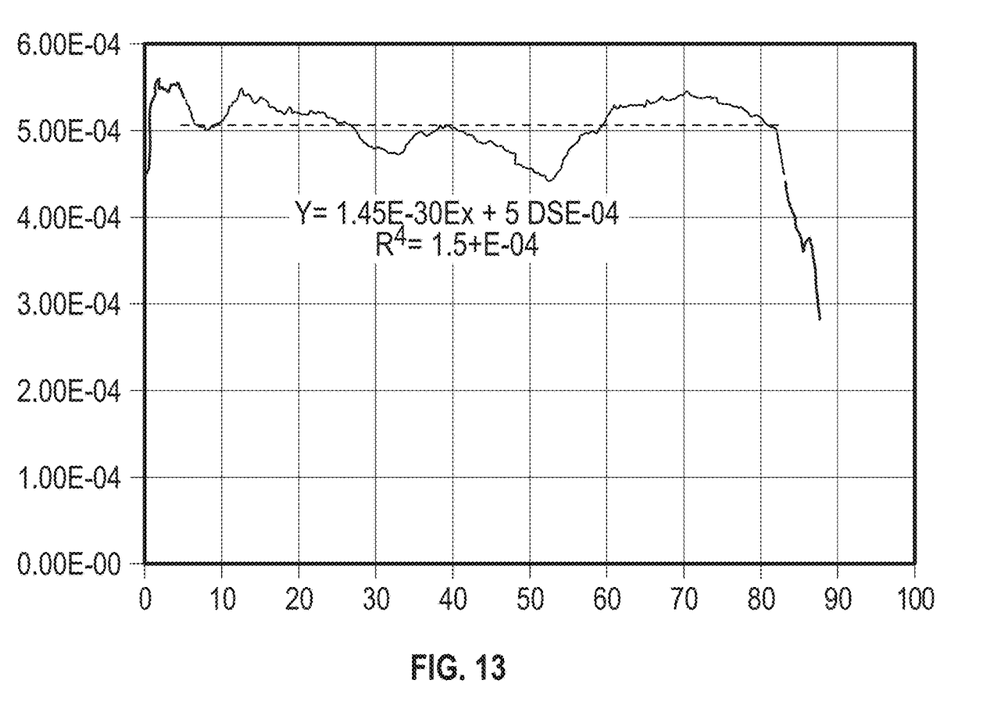
FIG. 13 is a graph showing relatively uniform illumination of the retina.

Referring to FIG. 11, a schematic of the model is illustrated. The schematic illustrates a single ray of light 74 coming from the light source 76 and bouncing off the inner surface of the contact lens 78. TIR may cause all the light to bounce off the inner surface or distal interface of the contact lens. Referring to FIG. 12, when TIR is achieved through use of implementations of contact lens assemblies 80 as described herein, the retina and other structures within the back inner surface of the eye 82 are well illuminated. Referring to FIG. 13, a graph illustrates relatively uniform illumination of a retina using implementations of flat lens assemblies as described herein.

Although the precursor of the inventive contact lens has been described as a "flat" lens, it may be beneficial to provide a slight curve on the distal surface of our contact lens. Such a curve enables a wider view of the eye's internal space.

The components used for illuminated contact lens assembly may be made of conventional materials used to make goods similar to these in the art, such as, by non-limiting example, glass, polymers, poly(methyl methacrylate), silicone, plastics, fiber optics, reflective materials, and LEDs. Those of ordinary skill in the art will readily be able to select appropriate materials and manufacture these products from the disclosures provided herein.

Ocular Imaging Camera

We have invented a new ocular imaging camera that is more suitable for front-line healthcare professionals to use and to share data with eye care specialists.

Currently preferred is a short cylindrical housing, mimicking a short pen for easy storage. Preferably there is a photosensor and lens in the low-lens camera subassembly end and a spacer between the housing and camera subassembly. Preferably the ocular imaging camera records multiple photos and even video that may provide more insight into the patient's current retinal status as well as the status of other ocular structures imaged with our camera.

Increasingly sensitive and smaller cameras are available, and our inventive ocular imaging camera will take advantage of those improvements. Moreover, these cameras are increasingly effective in low-light situations and will produce better ocular photos than previously available. These factors combine to produce better quality images, whether the patient provides an unsteady gaze or is very young.

The ocular imaging camera is digital for ease of transfer of images to computer for 1) enlarging, 2) professional analysis, 3) adding to patient files for comparison, etc. The ocular imaging camera has a server optionally programmed to detect whether a captured image has achieved the necessary quality standard for an eye care specialist and/or diagnostic algorithm to diagnose diabetic retinopathy and other retinal disorders. The algorithm is designed to run quickly and efficiently either in the camera or in the cloud so that health care providers are warned by light or sound within minutes (preferably seconds) in the event of poor image quality and need for images recapture. Preferably the images are recaptured within the same doctor visit and that only high-quality images undergo analysis. Real time feedback on captured images will increase the value to and confidence of health care professionals.

The digital ocular imaging camera is preferably WIFI competent to minimize weight. The inventive ocular imaging camera preferably has a battery for convenient use without cords getting in the way.

The inventive ocular imaging camera preferably has a housing that can sustain impact from accidental dropping in various clinic and emergency settings and from uncooperative patients. The more compact the ocular imaging camera is, the more convenient it is for use by health care professionals and paraprofessionals; this increases availability in a wider variety of settings from clinics to disaster zones.

The portable ocular imaging camera optionally offers good lighting for detailed views of the retina. Currently this is best provided with light-emitting diode (LED) lights that have the advantage of brightness with lower heat generation. The LED lights can be configured in a variety of ways, including but not limited to a) one or more pinpoint lights, b) a line of LED lights and/or c) a ring of LED lights within the lens portion of our design.

The LED lights are designed with enough power and aimed to provide adequate lighting of the retina, particularly the macula that only has a diameter of about 5.5 mm.

The System

As mentioned above, there will be tens of millions more AMD patients in the upcoming years—far more than current and future numbers of eye care providers available to adequately diagnose and sift through with traditional eye exams. After much thought, we invented a method to create a much more efficient way to connect the primary practitioner and the eye care specialist for earlier diagnosis. This method enables a retina specialist, ophthalmologist, optometrist ("eye care specialist") to diagnose hundreds of patients per hour.

The illuminated contact lens is placed on the patient's eyes, each one receiving a retinal photograph. Optionally the exterior of the eye and anterior segment are also photographed. Exterior photos will help explain quality limitations due to eyelid abnormalities or anterior segment opacities. The photographs and attendant patient information are transmitted to a central server and then fed to mobile devices of selected retina analysts, including but not limited to retina specialists, ophthalmologists, optometrists, etc. (eye care specialists). Programming appropriately identifies and arrays the photos.

Figure 14:
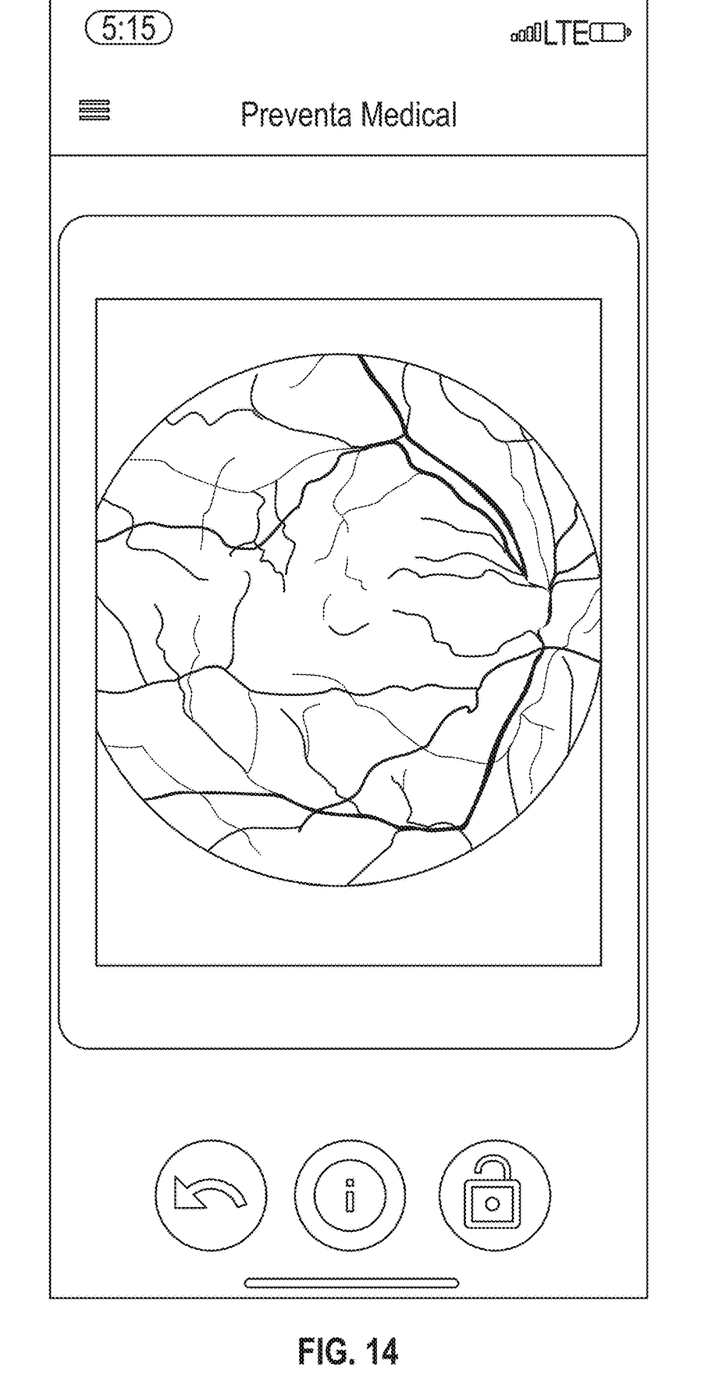
FIG. 14 is a schematic of a photograph of the retina with the controls at the bottom of the screen.

Eye care specialists are selected by their ability to differentiate normal from abnormal retina. The eye care specialist signs into the system. The mobile application (app) opens and automatically loads retinal images for rapid diagnosis (FIG. 14). The images are preferably displayed as a patient's right and left images. Preferably the first pair of images are of the eyes' exteriors. If those are normal, the specialist swipes left to see the interior images. The eye care specialist can quickly review those; most are normal as indicated by swipe gesture by the specialist, sending a signal to the server to send the patient and/or referring physician a letter indicating the absence of any serious abnormality. These steps are expected to take less than ten seconds of the eye care specialist's time. Preferably the analysis time ranges from one to thirty seconds, more preferably three to twenty seconds and most preferably eight to ten seconds. It should be understood that the actual time varies with pathology complexity, eye care specialist experience with the system, etc.

When the specialist observes eyes requiring follow-up, a swipe gesture forwards this decision to the server that in turn sends a letter to the patient and/or referring physician recommending follow-up.

In one embodiment, at the bottom of each image are three choices: 1) a side-sweep mark to expedite reporting the diagnosis of no pathology and follow up, 2) an information image and 3) a locking mechanism to permit viewing more data. The lock retains the present image and enables the specialist to magnify the image (zoom by pinching fingers on the screen or other convenient method). Enlarging specific areas enables an improved view of pathology. The image can also be swept directionally to pan over more of the surface of the retina, enabling the specialist to access all magnified areas of the photo in order to analyze the overall health of the eye and to locate problems in all imaged areas of the eye. Alternately the eye care specialist can expend the image with a double swipe or click or two fingers dragging parts of the image apart.

FIG. 15 displays a normal and abnormal image.

Figure 16:
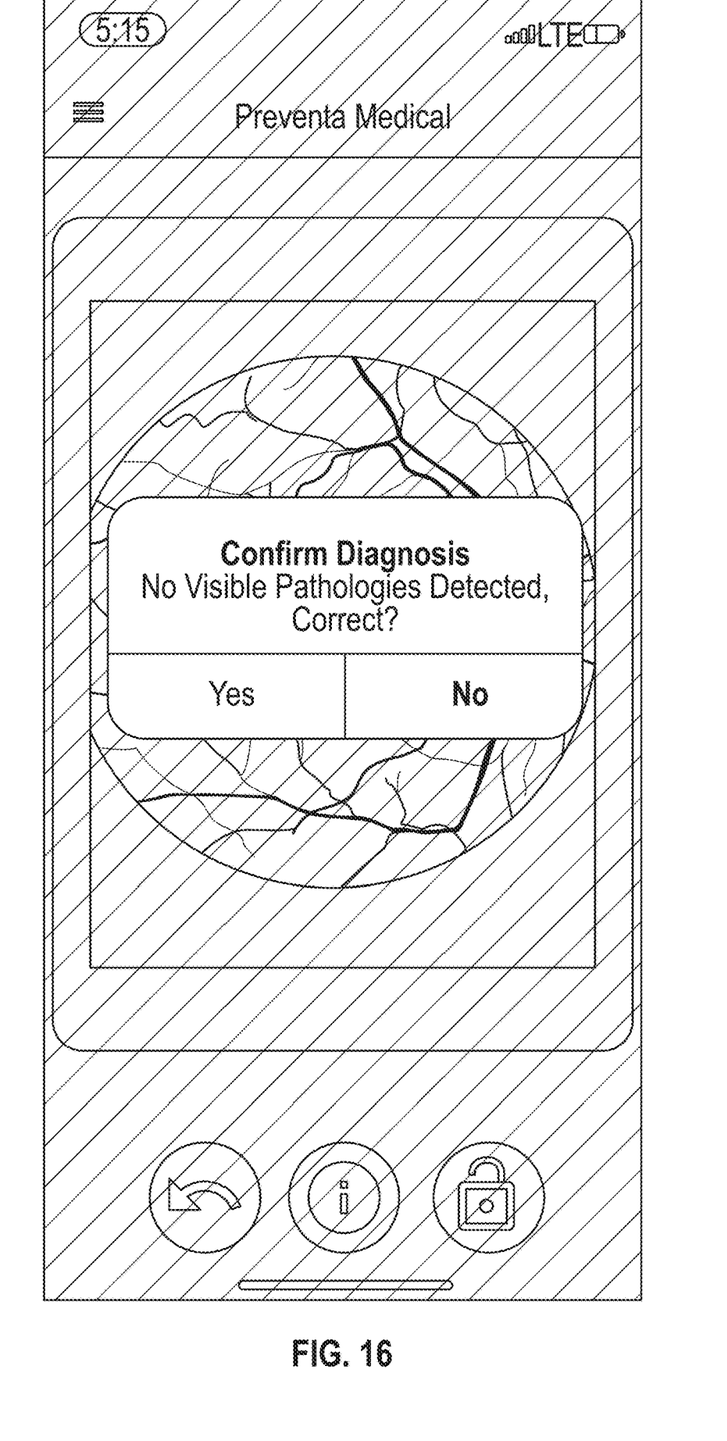
FIG. 16 shows the next screen in the app, in which the eye expert must confirm the previous decision.
Figure 151:
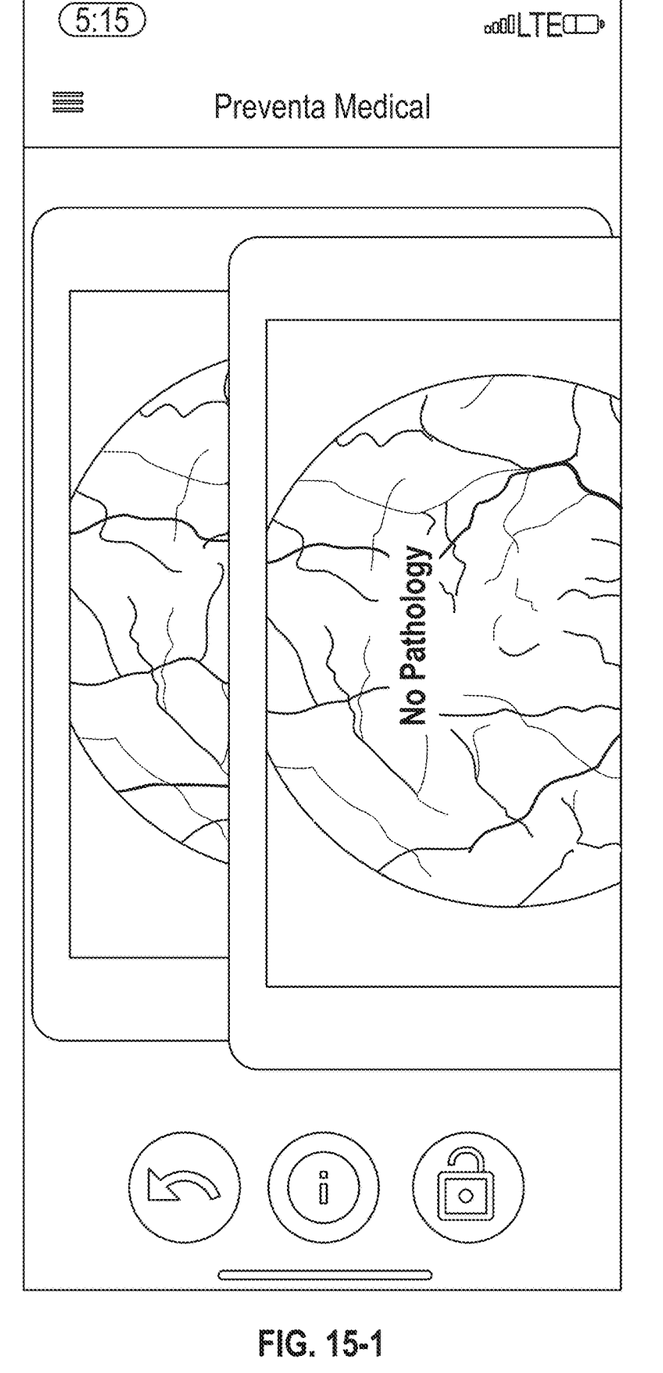
Figure 152:
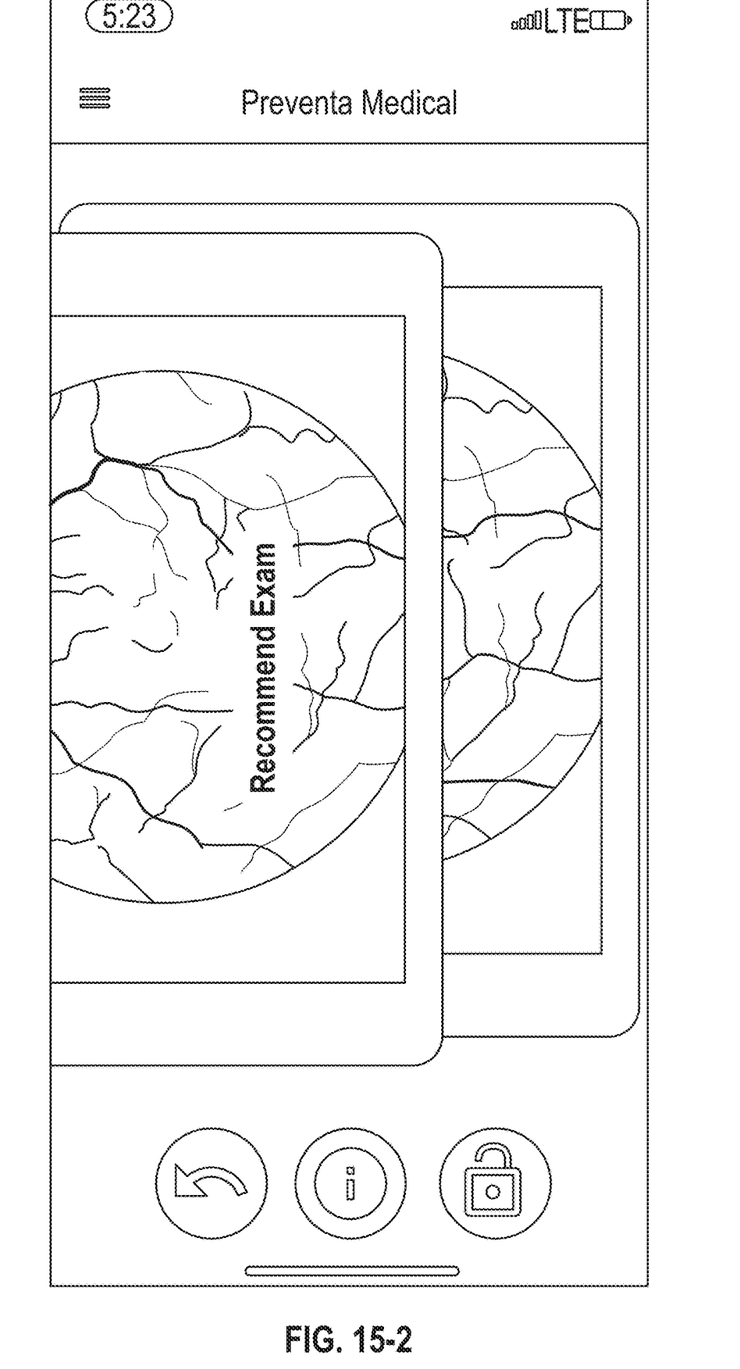

FIG. 16 shows a screen to confirm diagnosis with a "yes" or "no" button. Following this screen, specialists optionally enter other relevant clinical information including but not limited to age, degree of diabetic or hypertensive retinopathy, etc.

In another embodiment, retinal images for both left and right eyes for the same patient are displayed together on one screen.

The system automatically generates a report and forwards the report to the designated patient(s), primary care providers and/or other designated parties to inform them of the diagnosis. The system has a high level of security and complies with laws governing patient privacy.

Three service tiers are contemplated for the system, although fewer or more are possible. Specific activities can be assigned to different tiers.

Tier One is the screening level where the photos are reported as grossly normal or abnormal. This is a simple and efficient triage method that saves a physician office exam. Tier One is also amenable to a health optimization protocol, as it provides monitoring eye health well before the individual notices loss of vision. Abnormal blood vessels may be one such sign of developing hypertensive or diabetic retinopathy.

Tier Two provides the information of Tier One and more information, such as the diagnosis of the pathology.

Tier Three provides the information of Tier Two and more information, such as degrees of pathology and other specialist annotation and insights. This level may include degree of damage detected. For diabetic retinopathy, the specialist assigns a description of mild, moderate, and severe non-proliferative, as well as proliferative retinopathy; for hypertensive retinopathy, a standardized rating is assigned.

Tier Three also lends itself to monitoring of the progress of eye pathology. Preferably previous photos are compared with current photos, for example, by overlaying the previous and current images.

Tier Three activities also can be used for tracking the progression of other chronic diseases (i.e., diabetes and hypertension) because the blood vessels can be examined only in the retina.

While the server generates the report, the server pays specialists by any electronic banking app, and the next set of retinal images loads.

The invention has important advantages not only for patients, but also for physicians and healthcare systems. The patient's advantage is that this remote "initial visit" by the eye specialist can be done much earlier in the development of pathology, thereby enabling effective preventative steps, such as lifestyle modifications, earlier retinal intervention, etc. Furthermore, the patient foregoes the inconvenience and cost of an eye specialist visit, transportation there, and lost income. Additionally, patients and doctors can view all history of their retinal images on our secure web portal for education and patient progression monitoring.

Because diagnosis using our system takes up only a fraction of the specialists' time, the cost is accordingly only a fraction of a traditional eye exam. In addition, because the diagnosis can be done via mobile devices, including but not limited to a tablet, a smart phone and a virtual reality device, eye care specialists perform a "screening visit" at their convenience and anywhere. Major savings are brought to the eye care specialist when he is able to perform many more examinations without office and staff overhead cost. The eye care specialist's time and office can then be used for those cases truly requiring a traditional office visit.

The healthcare system benefits in that the "initial visit" is performed quickly and cost-effectively. Traditional office visits with general eye care specialists and retina specialists will become more streamlined and "High yield" as aforementioned.

Example 1

As mentioned above, the eye care specialist remotely using our system can often evaluate a retinal photo and make a gesture swipe or tap diagnosis efficiently, usually in less than ten seconds, particularly for a normal photo. Significantly abnormal photos can also take less than ten seconds, rapidly noted via swipe or tap and then categorized quickly again via swipe or tap. These correspond to Tiers One and Two above. If an eye care specialist can average one (or a right and left pair of) retinal evaluation(s) every ten seconds that translates into 6 patients/pairs of eyes per minute and 360 per hour. Assuming two hours of breaks to rest and six hours of active work time per day and five days a week of evaluations, each eye care specialist could conceivably evaluate 10,800 patients per week, or roughly 540,000 patients per year at a fraction of the cost of a traditional exam. Busy eye care specialists may see 50 patients a day in regular practice at traditional eye examinations in their practice at an annual rate of 12,500 patient visits per year. Many of these traditional visits are also repeat visits, making the efficiency of our proposed system stand out further. If AI were to eliminate the normal eyes from the pool of eyes to be evaluated, the specialist could read mostly pathology and efficiencies would grow even further.

Example 2

Busy eye care specialists will not need to dedicate their entire days to our system. Instead, a few hours a day suffice to make a significant difference—in between patients and during off hours. If each eye care specialist were to analyze retinal photos two hours per day (720) per weekday for 3,600 a week, and three hours on each weekend day (1,080) for 2,160 a weekend, each eye care specialist's evaluations total 288,000 patients per year.

In another embodiment, after the images clear the quality control image inspection (see the ocular imaging camera description) and are uploaded and transmitted, a diagnostic algorithm helps diagnose diabetic and hypertensive retinopathy and annotate the specific retinal features that prompted the diagnosis. Initially, we first use Artificial Intelligence to sort out images of healthy retinas as a pre-processing step before human readers. This is logical, since healthy eyes show less variability in appearance; hence "health" can be more accurately diagnosed by AI. As we build up a database of images, AI will develop to the point of diagnosing all images and rating the degree of diabetic and hypertensive retinopathy. We will compare human evaluations with the AI diagnosis to maintain quality control. Our system is not only an AI product but also includes human verification at all stages of development.

Additional options in the system include returning more detailed data to the data repository and sharing in more detail with the local physician.

The phones, tablets, virtual devices and other computerized devices used for this invention may be conventional models used to operate apps similar to these in the art, such as, by non-limiting example, smart phones, tablets and virtual reality devices. Those of ordinary skill in the art will readily be able to select appropriate materials and manufacture these products from the disclosures provided herein.

Many other diseases and syndromes affect the retina and can be efficiently evaluated by our devices and method. These include but are not limited to the aforementioned vascular disorders, inflammatory disorders, autoimmune disorders with possible associated eye findings, neoplastic disorders of the eye, glaucoma and other optic nerve anomalies, corneal disorders, disorders of the uvea, disorders of the crystalline lens and associated zonular apparatus, maculopathies, peripheral retinal degenerations, hereditary and congenital conditions with possible associated eye findings, infectious processes with possible associated eye findings, retinopathy of prematurity, neurologic disorders possibly manifesting with ocular findings, retinal tears, retinal detachments, phakomatoses, and other systemic disorders with possible associated eye findings, autoimmune disorders with possible associated eye findings, metabolic disorders with possible associated eye findings, degenerative disorders with possible associated eye findings, environmental or toxic conditions with possible associated eye findings. The implementations listed here, and many others, will become readily apparent from this disclosure. From this, those of ordinary skill in the art will readily understand the versatility with which this disclosure may be applied.

The pet market numbers in the tens of millions in the US alone. Work animals, such as dairy cows, are numerous. Both types of animals need inexpensive care. The disclosed contact lens, ocular imaging camera and system can be readily adapted for the pet and work animal market.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

The foregoing description is considered as illustrative only of the principles of the invention. Further, since numerous modifications and changes will readily occur to those skilled in the art, it is not desired to limit the invention to the exact creation and process shown and described above. Accordingly, all suitable modifications and equivalents may be resorted to falling within the scope of the invention.

For the purposes of promoting an understanding of the principles of the invention, the above Detailed Description and Examples represent exemplary embodiments, and specific language will be used to describe the same. It will nevertheless be understood that no limitation of the scope of the invention is hereby intended. Any alterations and further modifications of the inventive features illustrated herein, and any additional application of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," and "example," and similar language throughout this specification may, but do not necessarily, all refer to the same embodiment, to different embodiments, or to one or more of the figures. Additionally, reference to the words "embodiment," "example" or the like for two or more features, elements, etc., does not mean that the features are necessarily related, dissimilar, the same, etc.

Each statement of an embodiment or example is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional un-recited elements or method steps. "Comprising" is to be interpreted broadly and including the more restrictive terms "consisting of" and "consisting essentially of."

Reference throughout this specification to features, advantages, or similar language does not imply that all of features and advantages that may be realized with the present invention should be or are in any single embodiment of the invention. Rather, language referring to the features and advantages is understood to mean that a specific feature, advantage or characteristic described in connection with an embodiment is included in at least one embodiment of the present invention. Thus, discussion of the features and advantages, and similar language, throughout this specification may, but does not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized as certain embodiments that may not be present in all embodiments of the invention.

The invention claimed is:

1. An ocular contact lens comprising:
a curved surface on a first side;
a flat surface on a second side opposing the first side;
one or more chamfered edges between the first side and the second side wherein the one or more chamfered edges has a wider circumference closer to the curved surface and a narrower circumference near the flat surface; and
a straight edge between the curved surface and the one or more chamfered edges oriented perpendicular with the flat surface,
wherein, during use, the ocular contact lens is not fixedly coupled with an ocular imaging camera.

2. The ocular contact lens of claim 1, wherein the ocular contact lens comprises at least one of glass, polymers, poly(methyl) methacrylate, a coating, silicone, or plastics.

3. The ocular contact lens of claim 1, wherein an angle relative to the flat surface of the one or more chamfered edges is 0° to 90°.

4. The ocular contact lens of claim 1, wherein an angle relative to the flat surface of the one or more chamfered edges is 45°.

5. The ocular contact lens of claim 1, wherein the distal flat surface is slightly rounded to widen the view through the lens and allow for capture of a wider angle of the retina.

6. The ocular contact lens of claim 1, wherein a maximum feasible angle Θ relative to the flat surface for the one or more chamfered edges made of a contact lens material is determined by $\Theta < 180 - 2 \cdot \arcsin(1/n)$, wherein n is the refractive index of the contact lens material.

7. The ocular contact lens of claim 1, wherein a thickness between the curved surface and the flat surface is 0.25 mm to 2.75 mm.

8. The ocular contact lens of claim 1, wherein the one or more chamfered edges are one of straight or curved.

9. The ocular contact lens of claim 1, wherein a thickness between the curved surface the flat surface is 2.75 mm to 10 mm.

10. An ocular contact lens consisting essentially of:
a curved surface on a first side;
a flat surface on a second side opposing the first side;
one or more chamfered edges between the first side and the second side wherein the one or more chamfered edges has a wider circumference closer to the curved surface and a narrower circumference near the flat surface; and
a straight edge between the curved surface and the one or more chamfered edges of the ocular contact lens oriented perpendicular with the flat surface.

11. The ocular contact lens of claim 10, wherein the ocular contact lens comprises at least one of glass, polymers, poly(methyl) methacrylate, a coating, silicone, or plastics.

12. The ocular contact lens of claim 10, wherein an angle relative to the flat surface of the one or more chamfered edges is 0° to 90°.

13. The ocular contact lens of claim 10, wherein an angle relative to the flat surface of the one or more chamfered edges is 45°.

14. The ocular contact lens of claim 10, wherein the flat surface is slightly rounded to widen the view through the lens and allow for capture of a wider angle of the retina.

15. The ocular contact lens of claim 10, wherein a maximum feasible angle relative to the flat surface for the one or more chamfered edges made of a contact lens material is determined by $\Theta < 180 - 2 \cdot \arcsin(1/n)$, wherein n is the refractive index of the contact lens material.

16. The ocular contact lens of claim 10, wherein a thickness between the curved surface and the flat surface is 0.25 mm to 2.75 mm.

17. The ocular contact lens of claim 10, wherein the one or more chamfered edges are one of straight or curved.

18. The ocular contact lens of claim 10, wherein a thickness between the curved surface the flat surface is 2.75 mm to 10 mm.

19. An ocular contact lens consisting of:
a curved surface on a first side;
a flat surface on a second side opposing the first side;
one or more chamfered edges across a thickness of a material of the ocular contact lens between the first side and the second side wherein the one or more chamfered edges comprise an angle Θ relative to the flat surface; and
a straight edge between the curved surface and the one or more chamfered edges lens oriented perpendicular with the flat surface.

20. The ocular contact lens of claim 19, wherein a maximum feasible angle Θ relative to the flat surface for the one or more chamfered edges made of a contact lens material is determined by $\Theta < 180 - 2 \cdot \arcsin(1/n)$, wherein n is the refractive index of the contact lens material.

* * * * *

UNITED STATES PATENT AND TRADEMARK OFFICE
CERTIFICATE OF CORRECTION

| | |
|---|---|
| PATENT NO. | : 11,768,316 B2 |
| APPLICATION NO. | : 16/601442 |
| DATED | : September 26, 2023 |
| INVENTOR(S) | : Schadlu et al. |

It is certified that error appears in the above-identified patent and that said Letters Patent is hereby corrected as shown below:

In the Claims

Column 13, Line 1 of Claim 5 currently reads, --"...wherein the distal flat.."-- should read; "..wherein the flat.."

Signed and Sealed this
Fourteenth Day of November, 2023

Katherine Kelly Vidal
*Director of the United States Patent and Trademark Office*